United States Patent
Kraft et al.

(10) Patent No.: US 10,434,534 B2
(45) Date of Patent: Oct. 8, 2019

(54) APPLICATION SYSTEM COMPONENT WITH TRANSPONDER AND/OR WEAR DETECTION DEVICE

(71) Applicant: Dürr Systems AG, Bietigheim-Bissingen (DE)

(72) Inventors: Bernd Kraft, Steinheim-Höpfigheim (DE); Martin Stiegler, Beilstein (DE); Herbert Martin, Weinstadt (DE); Lothar Rademacher, Bietigheim-Bissingen (DE); Werner Schwager, Ludwigsburg (DE)

(73) Assignee: DÜRR SYSTEMS AG, Bietigheim-Bissingen (DE)

( * ) Notice: Subject to any disclaimer, the term of this patent is extended or adjusted under 35 U.S.C. 154(b) by 116 days.

(21) Appl. No.: 15/532,321

(22) PCT Filed: Nov. 23, 2015

(86) PCT No.: PCT/EP2015/002354
§ 371 (c)(1),
(2) Date: Jun. 1, 2017

(87) PCT Pub. No.: WO2016/087028
PCT Pub. Date: Jun. 9, 2016

(65) Prior Publication Data
US 2017/0259290 A1 Sep. 14, 2017

(30) Foreign Application Priority Data
Dec. 3, 2014 (DE) .......... 10 2014 017 895

(51) Int. Cl.
| B05B 15/00 | (2018.01) |
| B05B 12/00 | (2018.01) |
| B05B 12/08 | (2006.01) |
| B05C 19/00 | (2006.01) |

(Continued)

(52) U.S. Cl.
CPC ............ *B05B 15/00* (2013.01); *B05B 12/004* (2013.01); *B05B 12/08* (2013.01); *B05B 15/18* (2018.02);
(Continued)

(58) Field of Classification Search
CPC ....... B05B 15/00; B05B 15/18; B05B 12/004; B05B 12/08; B05B 1/044; B05B 13/0452;
(Continued)

(56) References Cited

U.S. PATENT DOCUMENTS

| 6,142,385 A | 11/2000 | Tacoma |
| 2003/0070414 A1* | 4/2003 | Pohn ........................ D01H 4/10 57/404 |

(Continued)

FOREIGN PATENT DOCUMENTS

| DE | 10 2004 014 209 A1 | 10/2005 |
| DE | 10 2005 049 436 A1 | 4/2007 |

(Continued)

OTHER PUBLICATIONS

International Search Report and Written Opinion for PCT/EP2015/002354 dated Jan. 29, 2016 (with English translation; 16 pages).

*Primary Examiner* — Leon Flores
(74) *Attorney, Agent, or Firm* — Bejin Bieneman PLC

(57) ABSTRACT

An application system component is provided in the form of a changeable application member such as a nozzle or a bell cup. The application system component includes a transponder for storing component data, from which the component data is readable, and a wear detection device for monitoring of the application system component. The wear detection device includes a wear mark and an optical detector.

18 Claims, 5 Drawing Sheets

Figure 1:
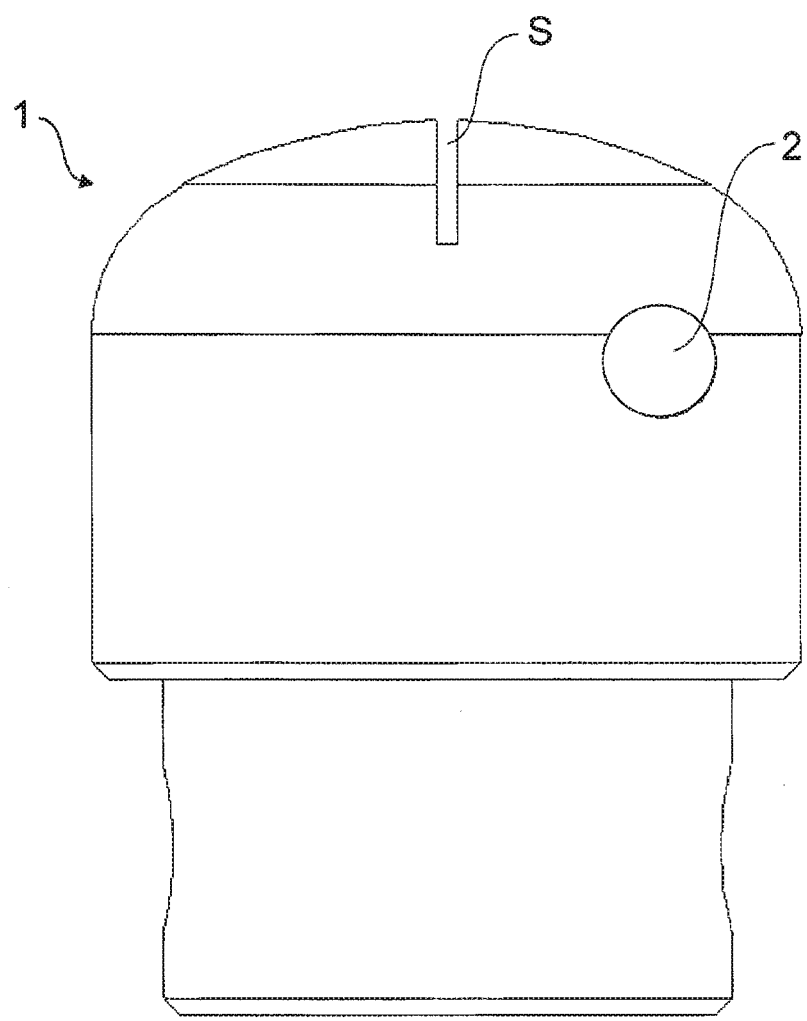

(51) Int. Cl.
  *G01N 21/88*   (2006.01)
  *B05B 15/18*   (2018.01)
  *B05B 1/04*    (2006.01)
  *B05C 5/02*    (2006.01)
  *B05C 11/10*   (2006.01)
  *B05B 13/04*   (2006.01)

(52) U.S. Cl.
  CPC ........... *B05C 19/008* (2013.01); *G01N 21/88* (2013.01); *B05B 1/044* (2013.01); *B05B 13/0452* (2013.01); *B05C 5/0216* (2013.01); *B05C 11/1002* (2013.01)

(58) Field of Classification Search
  CPC . B05C 19/008; B05C 5/0216; B05C 11/1002; G01N 21/88
  See application file for complete search history.

(56) References Cited

U.S. PATENT DOCUMENTS

| 2009/0223199 A1* | 9/2009 | Wassenhoven ......... D01H 1/16 57/362 |
| 2009/0285983 A1 | 11/2009 | Baldauf et al. |
| 2014/0113527 A1 | 4/2014 | Lindsay et al. |

FOREIGN PATENT DOCUMENTS

| DE | 20 2012 010 204 U1 | 1/2014 |
| EP | 1693560 A2 | 8/2006 |
| EP | 2839885 A1 | 2/2015 |
| WO | 2005075088 A2 | 8/2005 |
| WO | 2008022708 A1 | 2/2008 |
| WO | 2013158184 A1 | 10/2013 |

\* cited by examiner

APPLICATION SYSTEM COMPONENT WITH TRANSPONDER AND/OR WEAR DETECTION DEVICE

CROSS-REFERENCE TO RELATED APPLICATIONS

This application is a national stage of, and claims priority to, Patent Cooperation Treaty Application No. PCT/EP2015/002354, filed on Nov. 23, 2015, which application claims priority to German Application No. DE 10 2014 017 895.1, filed on Dec. 3, 2014, which applications are hereby incorporated herein by reference in their entireties.

BACKGROUND

The present disclosure relates to an application system component, in some implementations, a changeable application member, such as e.g. a changeable nozzle which is designed to apply an application material on workpieces, such as e.g. motor vehicle bodies and/or their attachments. The present disclosure further relates to an application system with a reading and/or writing device for data relating to the component.

Application system components, such as e.g. nozzles for the application of sealing material, bell cups for rotational atomisation of paint, as well as pumps and drive motors required for the application, are all subject to wear. Wear may lead to a number of problems in practice. Excessively worn application system components can result in the motor vehicle bodies being processed with inferior quality (e.g. inferior painting quality, inferior or less accurate sealing quality, etc.). Worn application system components should therefore be regularly exchanged, for which personnel and time are required which reduces the productivity of the application system. Moreover, changeover may also bring with it the risk that an error in the replacement process. Furthermore, wear usually occurs gradually and it may be difficult to determine with certainty whether the application system component is excessively worn. As such, it thus arises in practice that examinations are carried out without an excessively worn application system component ultimately being present. A further problem is that wear of the application system components often lies in the range of hundredths of a mm (1/100 mm range) so that precise detection of wear is only possible with great difficulty or not at all.

SUMMARY

The present disclosure provides an application system component, in some implementations, a changeable application member for application of an application agent on a workpiece, in particular motor vehicle bodies and/or their attachments. The application system component is thus in particular a component for an application system.

The application system component can be a changeable nozzle, e.g. for production of seam seals, flanged seam seals, protective films and/or visible seams on motor vehicle bodies and/or for preservation, in particular cavity preservation, of motor vehicle bodies. The application system component can alternatively or additionally be a changeable bell cup for application of paint on the workpiece.

In some implementations, the application system component is a component through which media can flow and/or a component which is affected by wear. Such an application system component has a transponder for storing component data and the component data are expediently readable in a contactless manner. Alternatively or additionally, the application system has a wear detection device for detecting (e.g. capturing) wear of the application system component.

In some implementations, the transponder and/or the component data can be used to identify the application system component and thus expediently differentiate it from other application system components. If the application system component is clearly identifiable, in particular additional component data (e.g. operating time, application agent throughput, etc.) can be assigned to the application system component, from which conclusions as to the wear and/or the history of the application system component can be drawn quasi indirectly. The transponder and/or the component data can thus be expediently used to determine the wear of the application system component quasi indirectly.

The wear detection device enables rapid and accurate detection of wear of the application system component, expediently detecting whether maximum admissible wear has been reached or not. As a result, e.g. even gradual wear processes can be detected.

In some implementations, the component data can be written to the transponder. Alternatively, the transponder can be only readable, and not writable. The transponder can thus be configured for bidirectional or for one-directional transmission of the component data.

In the context of the present disclosure, the component data may comprise component identification data (e.g. a serial number) for identification of the application system component so that the application system component can be clearly identified and thus differentiated from other application system components. In some implementations, the component data is exclusively component identification data.

According to the present disclosure, the component data can furthermore comprise component data for authentication of the application system component.

In some implementations, the application system component is made available with a separate reading and/or writing device. The reading and/or writing device expediently serves to read the component data from the transponder and/or for writing component data to the transponder.

In some implementations, the reading and/or writing device is configured for stationary mounting in an application system, while in other implementations the application system component is configured for movement with a manipulator. The manipulator is, in some implementations, a robot or a different motion automaton. The manipulator and the reading and/or writing device may be arranged in the application system so that the transponder can be positioned with the manipulator in front of the reading and/or writing device in order to be able to be read and/or written by the reading and/or writing device.

In some implementations, the application system component is made available with a separate control system. The control system can be connected to the reading and/or writing device e.g. wirelessly or by wired connection so that component data can be transmitted from the transponder via the reading and/or writing device to the control system and/or component data can be transmitted from the control system via the reading and/or writing device to the transponder.

In some implementations, the control system serves to control an operating process of the application system component and/or to control the manipulator for movement of the application system component.

Accordingly, in some implementations, component identification data is transmitted to the control system and the control system is configured to assign additional component data to the associated application system component (e.g. period of operation time, processed quantity (e.g. throughput) of application agent, starting time and/or end time of an operating process, etc.).

According to the present disclosure, the control system can furthermore be configured to compare component data assigned to a clearly identifiable application system component with expediently stored, predefined data, e.g. with setpoint, threshold and/or reference values and alternatively or additionally e.g. authentication data.

In some implementations of the present disclosure, the transponder has component identification data, and the other component data (e.g. period of operation, processed quantity (e.g. throughput) of application agent, starting time and/or end time of an operating process, etc.) is stored in the control system and processed in the control system (e.g. stored, monitored, compared and/or checked, etc.).

In some implementations, the control system is configured to generate a warning message and/or bring about an expediently automatic application system component changeover process if excessive wear of the application system component is concluded with the component data.

In some implementations, the control system is furthermore configured to generate a warning message and/or stop a processing process if an incorrect application system component is concluded with the component data.

The component data can include at least one of the following: the period of operation (e.g. the period of use) of the application system component, the quantity processed with the application system component (e.g. throughput) of application agent for application on the workpiece, the start time and/or the end time of an operating process of the application system component. The latter component data can, in some implementations, with the control system be assigned to a clearly identifiable application system component, from which in particular conclusions can be drawn as to the wear or generally to the history of the application system component. The latter component data are, in some implementations, stored in the control system, can alternatively or additionally also however be written to the transponder.

The transponder is, in some implementations, an RFID device (RFID: Radio-Frequency-Identification), in particular an RFID transponder.

The transponder is in some implementations configured to be read on an electronic basis and/or to be written on an electronic basis.

The transponder is mounted on or in the application system component.

In some implementations, the application system component has a clearance (e.g. a bore or a recess) in which the transponder is received, in some implementations, so that it does not impair the compactness of the application system component, it does not project from the outer surface of the body of the application system component and/or it is shaped flush with the outer surface of the application system component.

The transponder is, in some implementations, shaped and integrated into the application system component so that it does not impair or change the silhouette and/or outer base contour of the application system component.

The term "transponder" should be understood broadly in the context of the present disclosure and, in particular, comprises devices for storing component data, wherein the component data can be read in a contactless manner, wirelessly, by radio, optically and/or by infrared technology, and optionally can also be written thereon in the same manner.

The feature "control" should be understood broadly in the context of the present disclosure and can also encompass "regulation".

The wear detection device comprises at least one (e.g. circular, linear, rectangular, etc.) wear mark adjacent to a wear portion of the application system component, as a result of which the wear can be detected in particular visually and/or optically, e.g. by a controller, a camera or another optical detection instrument.

The at least one wear mark enables the wear detection device to detect and track the wear process, with, e.g., the optical detection instrument.

In some implementations, the wear detection device comprises at least one recessed wear mark (e.g. bore, recess, groove, hole, etc.) next to a wear portion of the application system component so that a sudden, e.g. jumpy change in operation is carried out if the wear portion widened by wear comes into contact with the recessed wear mark. It is alternatively or additionally possible that the wear detection device comprises at least one wear mark (e.g. bore, recess, groove, hole, etc.) filled with filling material next to a wear portion of the application system component so that the filling material escapes if it comes into contact with the wear portion widened by wear.

If the widened wear mark reaches the recessed wear mark, excess wear can be concluded.

In particular, the point in time when a maximum admissible wear is reached can be detected as a result of the at least one wear mark which is recessed and/or filled with filling material.

The filling material can be of a different colour to the application system component and/or the application material, as a result of which reaching of the wear mark(s) can be detected visually and/or optically e.g. on the application system component and/or the workpiece.

In some implementations, the filling material is liquid, in powder form and/or paste-like.

The wear detection device, in particular the wear detection mark(s), is, in some implementations, eroded, bored, cut and/or lasered (e.g. laser-engraved) into the body of the application system component.

The application system component is, in some implementations, a changeable nozzle for application of an application agent on motor vehicle bodies and/or their attachments.

The nozzle is, in some implementations, a flat stream nozzle and/or a nozzle with slot-shaped nozzle outlet opening. The nozzle can, however, also have different nozzle outlet forms.

The nozzle serves in particular to produce seals (e.g. seam seals and/or flanged seam seals), adhesive bonds, insulating elements, protective films and/or visible seams and indeed, in some implementations, on motor vehicle bodies and/or their attachments. The nozzle can alternatively or additionally serve the purpose of preserving, in particular the purpose of cavity preserving of motor vehicle bodies.

The above description relates to a single application system component. However, several application system components (e.g. of the same type and/or of different types) as described herein are generally used in an application system, hence the description also applies correspondingly to a plurality of application system components.

The present disclosure further relates to an operating method for an application system component, in some implementations, an application system component as disclosed herein. The operating method relates to the implementation "transponder" and comprises the step of reading component data from a transponder of an application system component, wherein the component data comprise at least component identification data for identification of the application system component so that the application system component can be clearly identified. Further method steps will become apparent from the disclosure relating to the application system component with transponder.

The present disclosure furthermore comprises an application system for applying an application agent on workpieces, e.g. motor vehicle bodies and/or their attachments, with at least one application system component as disclosed herein.

The application system generally comprises a plurality of application system components. In some implementations, application system components are of the same type (e.g. same design, same series, same purpose, etc.) and/or application system components are not of the same type (e.g. different design, different series, different purpose, etc.). The application system components nevertheless have in each case a transponder for storing component data, in particular component identification data so that the individual application system components can be clearly identified and can thus be expediently differentiated from one another.

The application system further comprises, in some implementations, at least one reading and/or writing device as disclosed herein for reading component data from the transponder and/or writing component data to the transponder and a control system as disclosed herein.

The application system furthermore has a manipulator, in particular a robot (e.g. a multi-axis articulated arm robot) which bears at least one application system component and can be configured to position the transponder for reading and/or writing in front of the reading and/or writing device.

The manipulator (e.g. robot) can, in the case of preferred exemplary implementations, bear at least two application system components oriented in different application directions with in each case a transponder. The robot can then be configured so that it reorientates itself in front of the reading and/or writing device so that the at least two transponders are readable and/or writable by the reading and/or writing device.

The application agent is, in some implementations, a sealing agent, a preservation agent (e.g. wax), an adhesive material, paint or plastic.

DRAWINGS

Figure 2:
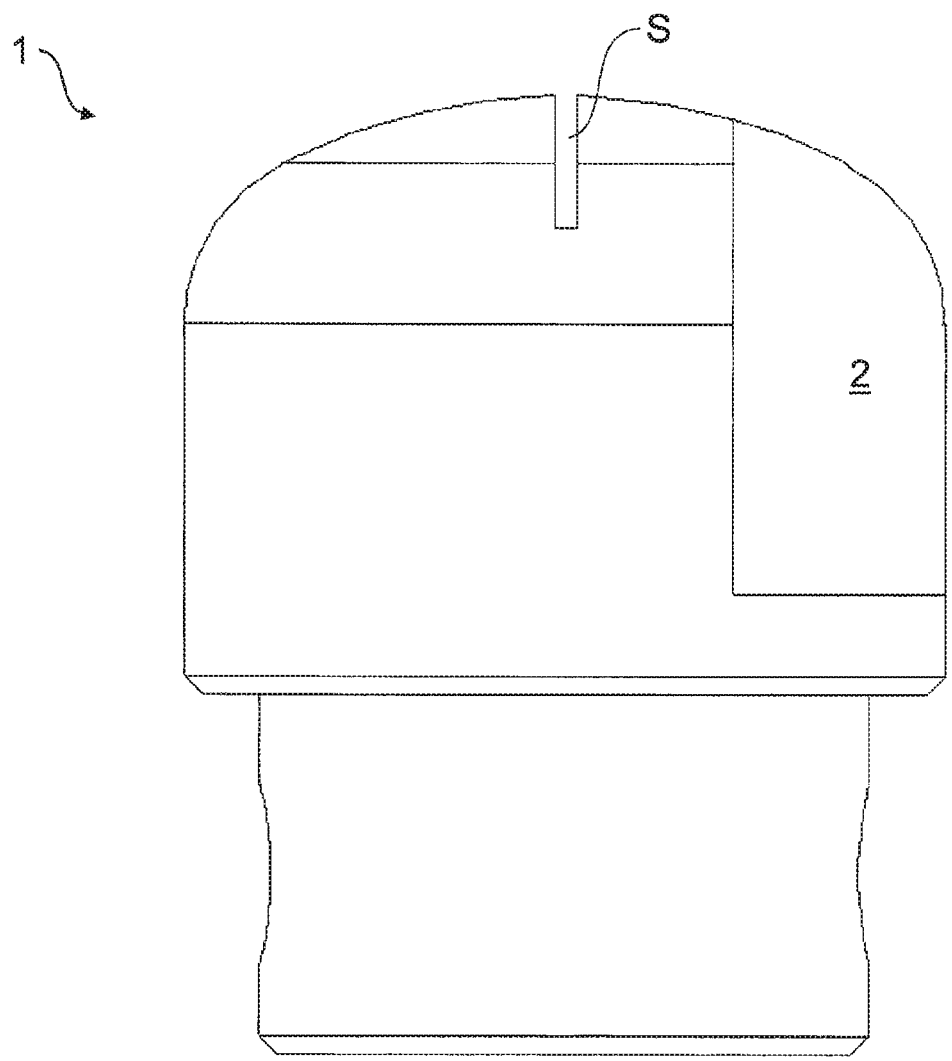
Figure 3:
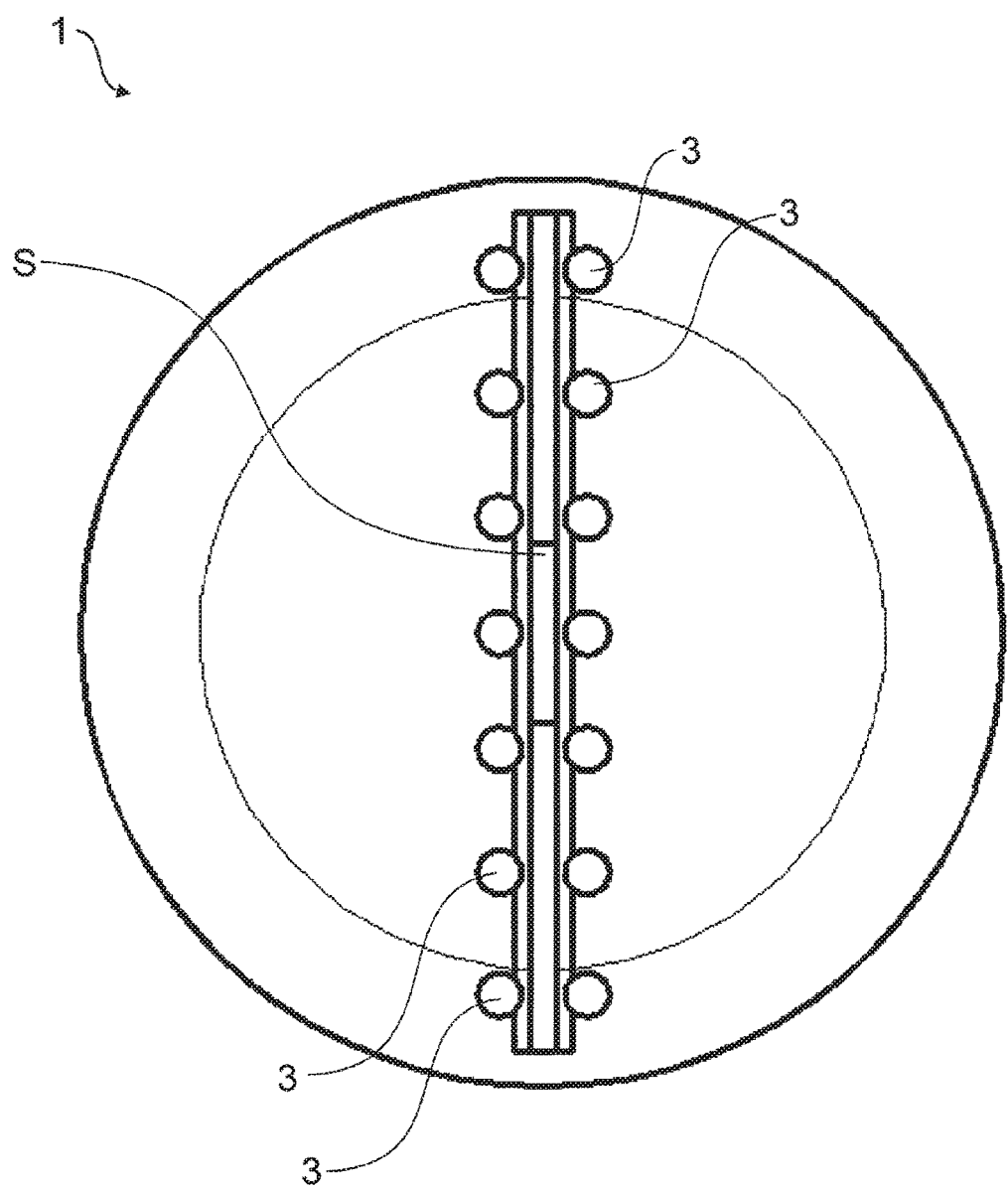
Figure 4:
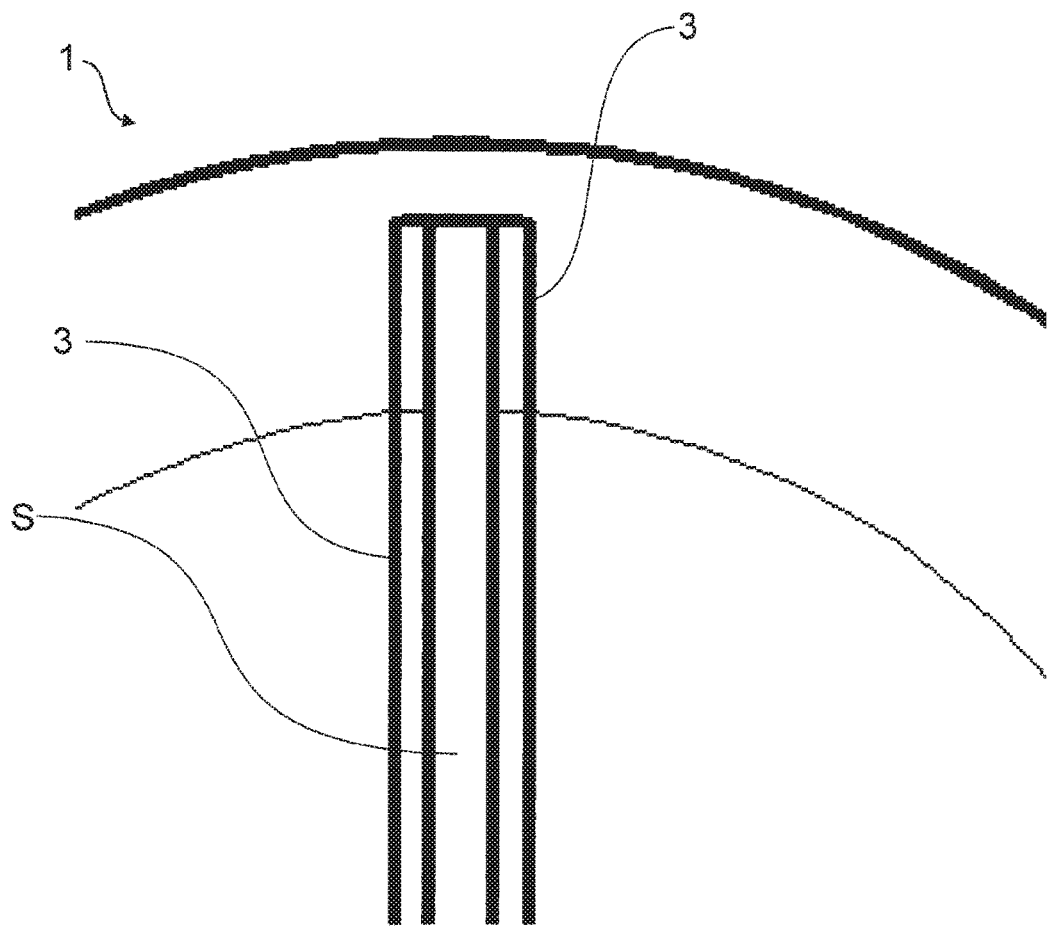
Figure 5:
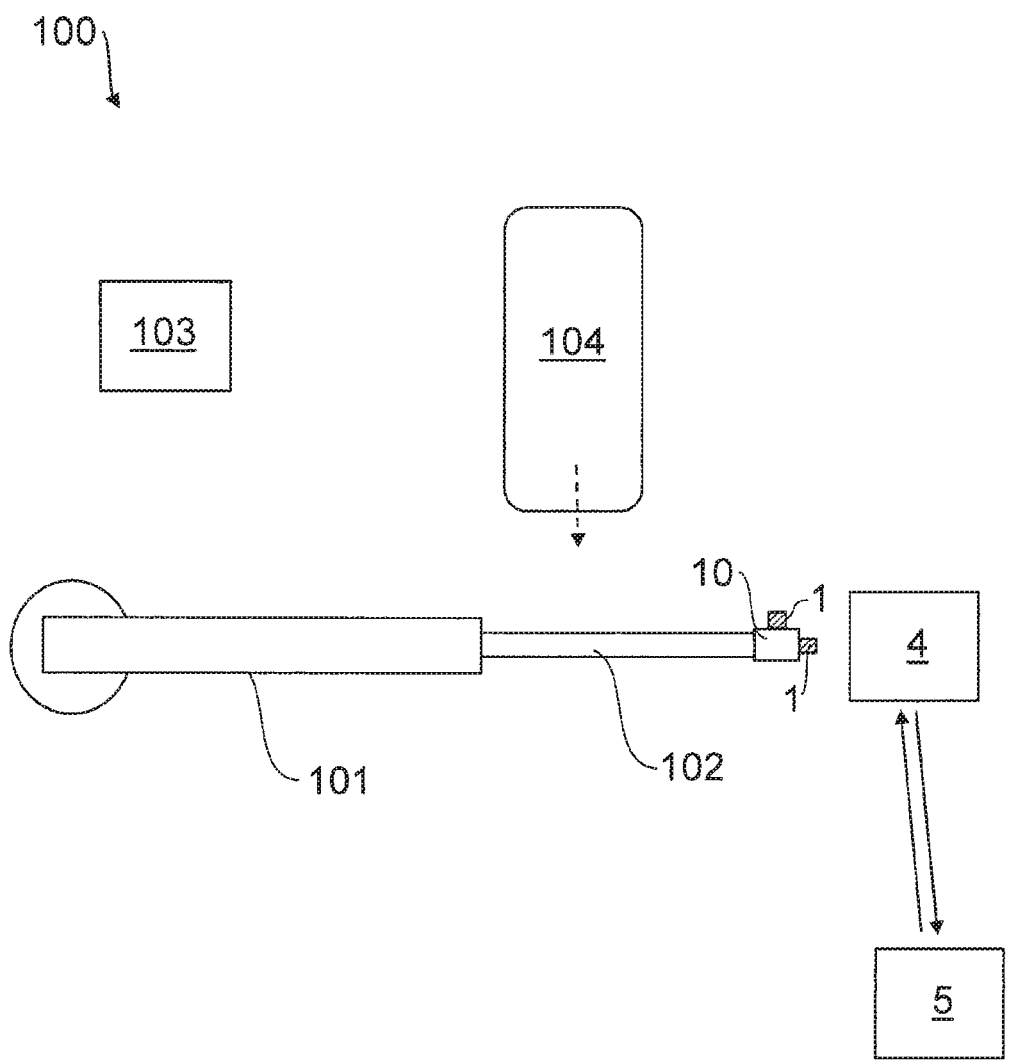

The present disclosure is described herein with reference to the figures, in which:

FIG. 1 shows a side view of an application system component according to one implementation of the present disclosure, FIG. 2 shows a side view of an application system component according to a different implementation of the present disclosure, FIG. 3 shows a top view of an application system component according to a different implementation of the present disclosure, FIG. 4 shows a top view of a partial section of an application system component according to an in turn different implementation of the present disclosure and FIG. 5 shows a schematic representation of an application system according to one implementation of the present disclosure.

The implementations shown in the figures partially correspond, wherein similar or identical parts are provided with the same reference numbers and for the explanation of which reference is also made to the description of the other implementations in order to avoid repetition.

DESCRIPTION

FIG. 1 shows a side view of an application system component 1 according to one implementation of the present disclosure.

Application system component 1 is a changeable nozzle for production of e.g. seam seals on motor vehicle bodies and is normally mounted on an application head of a lance which is rotatable about its longitudinal axis.

Nozzle 1 is a slotted nozzle (flatstream nozzle) with slot-shaped nozzle outlet opening S. Alternatively, nozzle 1 can be configured e.g. as a round nozzle with a round nozzle outlet opening.

Nozzle 1 is fitted with a transponder 2 on which in particular at least component identification data are stored and can be read in a contactless manner and to which component data can optionally be written in a contactless manner.

Transponder 2 is mounted in a receiving opening of nozzle 1 so that the compactness of nozzle 1 is not impaired by transponder 2. Transponder 2 is described in greater detail further below with reference to FIG. 5.

FIG. 2 shows a nozzle 1 according to a different implementation of the present disclosure.

One particular feature of nozzle 1 shown in FIG. 2 is that it has a relatively large clearance in comparison to FIG. 1 for integration of transponder 2. It is particularly advantageous therein that the reading and/or writing of transponder 2 is hindered to a lesser extent by the usually metallic nozzle body. Transponder 2 of FIG. 2 is thus axially and laterally readable and optionally writable, while transponder 2 of FIG. 1 is only laterally readable.

FIG. 3 shows a top view of an application system component 1 according to a different implementation of the present disclosure.

Application system component 1 is again a slotted nozzle as in FIGS. 1 and 2.

However, nozzle 1 of FIG. 3 comprises a mechanical wear detection device 3 for detecting wear of nozzle 1, in particular of the slot-shaped nozzle outlet opening S.

Wear detection device 3 comprises a plurality of recessed wear marks (for the purpose of illustration, only four are provided with reference number 3 in FIG. 3) next to the wear portion of nozzle 1, i.e. next to slot-shaped nozzle outlet opening S.

If slot-shaped nozzle outlet opening S is widened by wear to such an extent that it reaches at least one of wear marks 3, a sudden, disproportionate rise in material consumption and/or a falling application pressure arise(s). It can be ascertained from this that nozzle 1 has reached a degree of wear in order to be replaced.

It is optionally possible to fill recessed wear marks 3 with filling material. The filling material escapes if it comes into contact with wear portion S widened by wear. The filling material can be liquid, in powder form or paste-like, is, however, in some implementations, liquid plastic. The filling material can furthermore be of a different colour to the colour of nozzle 1 and/or to the colour of the application material so that reaching of maximum admissible wear can be detected not only at nozzle 1 itself, but also e.g. on the workpiece to be processed, i.e. generally a motor vehicle body, and nozzle 1 itself.

FIG. 4 shows a partial portion of a nozzle 1 according to a different implementation of the present disclosure.

One particular feature of nozzle 1 shown in FIG. 4 is that it has, in addition to slot-shaped nozzle outlet opening S, wear marks 3 which are eroded into the nozzle body, in particular laser-engraved, linear wear marks 3 which serve the purpose of visual or optical inspection of wear. Individual wear marks 3 characterise different wear stages so that e.g. when the first wear stage is reached there is still no immediate need for replacement, but nozzle 1 is characterised as ready for replacement in the near future. The next wear stage can then characterise nozzle 1 as ready for replacement.

FIG. 5 shows a schematic representation of an application systems 100 according to one implementation of the present disclosure.

Application system 100 comprises a robot (manipulator) 101 which bears a lance 102 which is rotatable about its longitudinal axis. An application head 10 with three changeable nozzles 1 oriented in different application directions is mounted on lance 102, of which only two can be seen in FIG. 5.

Nozzles 1 serve e.g. to produce seam seals on motor vehicle bodies 104 and are subject to wear as a result of the application agent and the associated abrasiveness.

Nozzles 1 are fitted with transponders 2 on which nozzle identification data are stored so that the individual nozzles 1 can be clearly identified and consequently differentiated from one another. In the case of the implementation shown in FIG. 5, transponders 2 are only readable and not writable.

Application system 100 further comprises a reading device 4 for reading nozzle identification data from the transponders 2 of the individual nozzles 1. Reading device 4 serves the purpose of data communication with a control system 5 for controlling the application processes of nozzles 1 and of robot 101.

In the case of the exemplary implementation under consideration, robot 101 is configured so that it moves application head 10 in front of reading device 4 at predefined intervals (e.g. before and/or after a motor vehicle body) and reorientates itself so that the nozzle identification data of the individual transponders 2 can be read and transmitted to control system 5.

A check can e.g. be performed thereupon in control system 5 as to whether correct nozzles 1 are mounted on application head 10 for the upcoming application process.

In control system 5, additional nozzle data, e.g. the start time and the end time of the application processes of the individual nozzles 1, the period of operation of the individual nozzles 1, the quantity applied with the individual nozzles 1 (e.g. throughput) of application agent, etc., can furthermore be assigned to the individual nozzles 1 which are clearly identifiable as a result of the nozzle identification data. Conclusions as to the wear of the individual nozzles 1 can then be drawn quasi indirectly from the latter nozzle data. If a specific nozzle 1 has applied e.g. a predefined application agent quantity or there has been operation for a predefined period of operation, control system 5 can issue a warning message and/or initiate a, in some implementations, automatic nozzle changeover process.

Transponders 2 thus lead in two ways to an improvement in process and product reliability. On one hand, because changeable application system components 1 can be clearly identified and thus checked for correctness in relation to the upcoming processing process. On the other hand, because component data can be assigned concretely to clearly identifiable application system components, from which e.g. conclusions can be drawn as to the wear and the history thereof.

Application system 100 can furthermore have an optional nozzle changing station 103 with a plurality of nozzles 1. Robot 101 can in this case be configured so that it guides application body 10 for automatic changeover of nozzles 1 to nozzle changing station 103, where the nozzle changeover takes place automatically. The nozzle changeover of nozzles D1 is therefore not carried out manually, but rather automatically via robot 101 and nozzle changing station 103. If application system 100 has a nozzle changing station 103, reading device 4 can be mounted at nozzle changing station 103 or at least adjacent thereto.

Reading device 4 can also be configured as a reading and writing device in order to write component data to the individual transponders 2.

The application system component is indeed, in some implementations, a nozzle 1, but can also comprise other application members, e.g. bell cups, and other components which are commonplace in application systems and are subject to wear.

As mentioned above, in the case of the described exemplary implementation, reading and/or writing device 4 can be arranged at or in the vicinity of a nozzle changing station 103, i.e. generally in a stationary manner at one point of an application system which application robot 101 must in any case approach on a regular basis so that the, in some implementations, automatic reading or writing of the component data can be carried out without particular movement and time outlay. Another such point of the application system would be, for example, also a cleaning station for regular automatic cleaning of the application members.

Exemplary implementations of the present disclosure are also include implementations in which the reading and/or writing device does not have to be arranged in a stationary manner, but rather can be moved in order to be positioned in front of the transponder of an application robot.

For example, the reading and/or writing device are moved in such implementations with the aid of a separate handling robot or in special cases also manually.

In other implementations, instead of a separate handling robot for the reading and/or writing device, the respective reading and/or writing devices are respectively arranged on at least one or several or all application robots e.g. of a typical coating system for serial coating of motor vehicle bodies themselves. Each of a plurality of application robots can then initiate the desired reading or writing process by moving its transponder near to the reading and/or writing device of a different application robot or by moving its reading and/or writing device near to the transponder of a different application robot. The application robots can, in the case of this example, therefore supply one another with the desired component data, wherein it would, for example, also be possible that a given application robot reads the component data of a second robot and transfers its own data to a third robot. The data transfer can then be carried out expediently in each case if the relevant robots move close to another in any event as programmed during application operation. The reading or writing processes and the robot movements can also be controlled in all the stated cases by the mentioned control system.

The present disclosure is not restricted to the preferred implementations described above. On the contrary, a plurality of variants and modifications are possible which also make use of the principles of the present disclosure.

The invention claimed is:

1. A component for an application system, the component being an application member of the application system, the component comprising:
   a transponder configured for storing component data, the component data being configured to be readable; and
   a wear detection device configured to identify wear of the component, the wear detection device including at least one wear mark at a wear portion of the component and an optical detector.

2. The component of claim 1, wherein the transponder is writable with component data.

3. The component of claim 1, wherein the transponder is not writable.

4. The component of claim 1, wherein the component data includes a least component identification data for the component.

5. The component of claim 1, wherein the component data includes at least component data for authentication of the component.

6. The component of claim 1, wherein the transponder is in communication with a separate device configured to at least one of read component data from the transponder and write component data to the transponder.

7. The component of claim 1, wherein the transponder is an RFID transponder.

8. The component of claim 1, wherein the transponder is mounted to the application system component.

9. The component of claim 1, wherein the application system component has a clearance and the transponder is integrated into the clearance at least flush with an outer surface of the application system component.

10. The component of claim 1, wherein the wear detection device includes at least one recessed wear mark next to the wear portion the component.

11. The component of claim 1, wherein the wear detection device includes at least one wear mark filled with filling material to the wear portion of the component, the filling material configured to escape with a predetermined amount of wear.

12. The component of claim 1, wherein the filling material is a different color than the component.

13. A system for application of a material on workpieces, the system comprising:
    at least one application system component having a transponder configured for storing component data, the component data being configured to be readable;
    a wear detection device configured to identify wear of the component, the wear detection device including at least one wear mark at a wear portion of the component and an optical detector;
    a communication device coupled to the transponder and configured to at least one of read and write the component data on the transponder; and
    a control system communicatively coupled with the transponder by the communication device.

14. The system of claim 13, wherein the component data includes at least one of a start time of an operating process of the application system component, an end time of the operating process, a duration of the operating process, and a quantity of application material processed with the application system component.

15. The system of claim 13, wherein the control system is configured to at least one of generate a warning message and initiate an application system component changeover process if excessive wear of the application system component is detected.

16. The system of claim 13, wherein the control system is configured to at least one of generate a warning message and stop an operating process if an incorrect application system component is detected.

17. The system of claim 13, further comprising a manipulator bearing the application system component, the manipulator being configured to position the component with the transponder for access by the communication device.

18. The system of claim 13, further comprising a manipulator configured to position the reading and/or writing device for reading and/or writing in front of the transponder.

* * * * *